(12) United States Patent
Grez (10) Patent No.: US 10,518,097 B2
(45) Date of Patent: Dec. 31, 2019

(54) WORKPIECE WITH INTEGRATED BATTERY

(71) Applicant: L'Oreal, Paris (FR)

(72) Inventor: Joseph W. Grez, North Bend, WA (US)

(73) Assignee: L'Oreal, Paris (FR)

( * ) Notice: Subject to any disclaimer, the term of this patent is extended or adjusted under 35 U.S.C. 154(b) by 923 days.

(21) Appl. No.: 14/144,035

(22) Filed: Dec. 30, 2013

(65) Prior Publication Data

US 2015/0182290 A1   Jul. 2, 2015

(51) Int. Cl.
*A46B 13/02* (2006.01)
*A61N 2/00* (2006.01)
(Continued)

(52) U.S. Cl.
CPC .............. *A61N 2/002* (2013.01); *A46B 13/02* (2013.01); *A46B 15/003* (2013.01); *A46B 15/0034* (2013.01); *A61F 7/00* (2013.01); *A61F 7/007* (2013.01); *A61M 37/0092* (2013.01); *A61N 1/30* (2013.01); *A61N 1/325* (2013.01); *A61N 1/40* (2013.01); *A61N 2/00* (2013.01); *A46B 2200/102* (2013.01); *A61F 2007/008* (2013.01);
(Continued)

(58) Field of Classification Search
CPC ...... A61H 23/02; A46B 13/02; A46B 15/002; A46B 15/003; A46B 15/0034; A46B 2200/102; A61N 2/002; A61N 1/30; A61N 1/325; A61N 1/40; A61N 2/00; A61N 5/0616; A61N 2005/0644; A61F 7/00; A61F 7/007; A61F 2007/0078; A61F 2007/008; A61M 37/0092

USPC .............................. 15/28; 601/72, 2, 70, 138
See application file for complete search history.

(56) References Cited

U.S. PATENT DOCUMENTS 3,585,990 A * 6/1971 Blachly .............. A61H 23/0263
601/72
5,500,971 A * 3/1996 Springmann .......... A46B 13/02
15/23

(Continued)

FOREIGN PATENT DOCUMENTS

EP       1 525 872 A1    4/2005
JP       06-315413 A     11/1994
(Continued)

OTHER PUBLICATIONS

International Preliminary Report on Patentability dated Jul. 14, 2015, issued in corresponding International Application No. PCT/US2014/063216, filed Oct. 30, 2014, 8 pages.

(Continued)

Primary Examiner — Robert J Scruggs
(74) Attorney, Agent, or Firm — Christensen O'Connor Johnson Kindness PLLC (57) ABSTRACT

A workpiece, such as a treatment workpiece, for use with a non-powered appliance is disclosed. The workpiece includes a rechargeable or non-rechargeable battery integrated into the workpiece housing. The workpiece in some examples can be configured such that the battery is neither removable nor replaceable. The capacity of the battery can either be selected so as to provide at least a single use of the workpiece or to correspond to the recommended replacement period (e.g., 90 days) of the workpiece.

17 Claims, 5 Drawing Sheets

(51) Int. Cl.
*A61M 37/00* (2006.01)
*A61F 7/00* (2006.01)
*A61N 1/32* (2006.01)
*A46B 15/00* (2006.01)
*A61N 1/30* (2006.01)
*A61N 1/40* (2006.01)
*A61N 5/06* (2006.01)

(52) U.S. Cl.
CPC ..... *A61F 2007/0078* (2013.01); *A61N 5/0616* (2013.01); *A61N 2005/0644* (2013.01)

(56) References Cited

U.S. PATENT DOCUMENTS

| | | | |
|---|---|---|---|
| 6,879,818 B2* | 4/2005 | Wageneck | H04R 5/023 |
| | | | 4/597 |
| 7,282,036 B2* | 10/2007 | Masuda | A61H 23/0263 |
| | | | 601/138 |
| 2006/0094992 A1* | 5/2006 | Imboden | A61H 19/00 |
| | | | 601/70 |
| 2008/0262581 A1 | 10/2008 | Barsness et al. | |
| 2013/0046212 A1* | 2/2013 | Nichols | A46B 7/04 |
| | | | 601/18 |
| 2015/0005681 A1 | 1/2015 | Gimelli et al. | |

FOREIGN PATENT DOCUMENTS

| | | |
|---|---|---|
| JP | 2005124893 A | 5/2005 |
| JP | 2008-539882 A | 11/2008 |
| JP | 2010-509900 A | 4/2010 |
| JP | 2013-223717 A | 10/2013 |
| WO | 2006-119376 A2 | 11/2006 |
| WO | 2013/107625 A2 | 7/2013 |
| WO | 2013107635 A2 | 7/2013 |

OTHER PUBLICATIONS

International Search Report dated Jan. 21, 2015, issued in corresponding International Application No. PCT/US2014/063221, filed Oct. 30, 2014, 3 pages.
Written Opinion dated Jan. 21, 2015, issued in corresponding International Application No. PCT/US2014/063221, filed Oct. 30, 2014, 7 pages.
Notification of Reasons for Refusal issued in corresponding Japanese Application No. 2016-544093, filed Oct. 30, 2014, 6 pages.
Office Action dated Nov. 27, 2017, issued in corresponding Chinese Application No. 201480071522.9, filed Oct. 30, 2014, 22 pages.
Third Office Action dated Jun. 14, 2018, Issued in corresponding Chinese Application No. 201480071522.9, filed Oct. 30, 2014, 12 pages.
Notification of Reasons for Refusal, dated Jun. 11, 2018, Issued in corresponding Japanese Application No. 2016-544093, filed Oct. 30, 2014, 4 pages.

* cited by examiner

WORKPIECE WITH INTEGRATED BATTERY

BACKGROUND

Conventional skin care devices typically contain a treatment workpiece coupled to a personal care appliance. The personal care appliance includes an integrated rechargeable battery that provides power to the device for a number of treatment cycles. This battery has always been internal to the handle of the appliance, which is permanently sealed. As a result, after the contained rechargeable battery is drained, the device requires recharging by means of a wall charger or the like.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In accordance with aspects of the present disclosure, a workpiece for use with a non-powered appliance is provided. The workpiece includes a housing, a battery carried by the housing, a treatment applicator, and an electrical interface carried by the housing. In some embodiments, the electrical interface is configured to be electrically coupled to the non-powered appliance for supplying power thereto.

In accordance with another aspect of the present disclosure, an apparatus is provided. The apparatus includes a non-powered appliance including a drive motor and a workpiece electrical interface, and a workpiece selectively mounted to the non-powered appliance. In some embodiments, the workpiece includes a treatment applicator, a battery, and an electrical interface configured to be coupled to the workpiece electrical interface when the workpiece is mounted to the non-powered appliance for supplying power from the battery to the drive motor.

In accordance with another aspect of the present disclosure, a system is provided. The system includes a charger that includes a workpiece interface for selectively mounting a workpiece, an electrical outlet interface configured to receive power from an electrical outlet, and a workpiece electrical interface coupled to the electrical outlet interface. The system also includes a workpiece selectively mountable to the charger. In some embodiments, the workpiece includes a treatment applicator, a battery, and an electrical interface coupled to the battery. The electrical interface is configured to be coupled to the workpiece electrical interface of the charger when the workpiece is mounted to the charger in order to supply recharge power from the charger to the battery.

DESCRIPTION OF THE DRAWINGS

The foregoing aspects and many of the attendant advantages of the disclosed subject matter will become more readily appreciated as the same become better understood by reference to the following detailed description, when taken in conjunction with the accompanying drawings, wherein.

DETAILED DESCRIPTION

The detailed description set forth below in connection with the appended drawings where like numerals reference like elements is intended as a description of various embodiments of the disclosed subject matter and is not intended to represent the only embodiments. Each embodiment described in this disclosure is provided merely as an example or illustration and should not be construed as preferred or advantageous over other embodiments. The illustrative examples provided herein are not intended to be exhaustive or to limit the claimed subject matter to the precise forms disclosed.

The following discussion provides examples of devices that relate to personal care, and more particularly, to treatment workpieces that incorporate a power source, such as a battery. The examples of the treatment workpieces can be configured to be selectively attached to a motorized, but powerless, personal care appliance (hereafter referred to as a non-powered appliance). As will be described in more detail below, the treatment workpieces set forth herein, when coupled to the non-powered appliance, provide power thereto. Together, embodiments of the treatment workpiece and the non-powered appliance aim to provide, for example, an oscillating, reciprocating, and/or rotational motion for treatment, such as skin cleaning, massaging, or exfoliating of a subject's skin, etc. Other embodiments of the treatment workpiece and the non-powered appliance additionally or alternatively aim to provide, for example, light, sound, heat, magnetic or RF treatment, iontophoresis, phonophoresis, just to name a few.

Although some examples of the present disclosure may be described hereinafter with reference to treatment workpieces, it will be appreciated that aspects of the present disclosure have wide application, and therefore, may be suitable for use with many other workpieces, including workpieces of the non-treatment type. Accordingly, the following descriptions and illustrations herein should be considered illustrative in nature, and thus, not limiting the scope of the claimed subject matter.

As will be described in more detail below, instead of a power source being located within the personal care appliance, examples of the treatment workpieces disclosed herein provide a rechargeable or non-rechargeable battery integrated into the workpiece housing.

The workpiece in some embodiments is configured such that the battery is neither removable nor replaceable. In some embodiments, the capacity of the battery is such so as to provide at least a single use of the workpiece, and can be recharged quickly (e.g., three (3) minutes or less). In these embodiments and others, the workpiece may provide for easy replacement after the battery's charging life cycle is complete. In other embodiments, the battery has a large, non-rechargeable capacity that can correspond to the recommended replacement period (e.g., 90 days) of the workpiece.

As used herein, the battery may include, but is not limited to, a device that stores electrical energy, converts stored energy into electrical energy and/or generates electrical energy. For example, the term battery may include a capacitor, a bank of capacitors, a condenser or a bank of condensers, which store electric potential. In another example, the term battery may include a dry chemical cell(s), such as a conventional alkaline battery, nickel-cadmium (NiCd) battery, nickel-metal hydride (NiMH) battery, or a lithium-ion (Li-ion) battery, etc., or may include a wet cell(s), such as a conventional lead-acid cell battery, which converts energy stored in a chemical form into electrical energy. In a further example, the term battery may include a fuel cell that generates electrical energy via a chemical process between a fuel (e.g., hydrogen) and an oxidant. The term battery also includes a single cell as well as multiple cells, regardless of whether the cells are located in the same or separate housings.

As will be also described in more detail below, embodiments of the present disclosure may include a charger configured to interface with the workpiece and with mains power, such as an electrical wall outlet, for recharging the battery of the workpiece. The charger in some embodiments is directly coupled to the electrical wall outlet and provides a socket or other suitable mechanical and electrical interface in order to physically mount the workpiece to the charger and to transfer mains power to the workpiece for battery recharging. As will be further described in detail below, recharging of the battery may also provide workpiece drying.

In the following description, numerous specific details are set forth in order to provide a thorough understanding of one or more embodiments of the present disclosure. It will be apparent to one skilled in the art, however, that many embodiments of the present disclosure may be practiced without some or all of the specific details. Further, it will be appreciated that embodiments of the present disclosure may employ any combination of features described herein.

Figure 1:
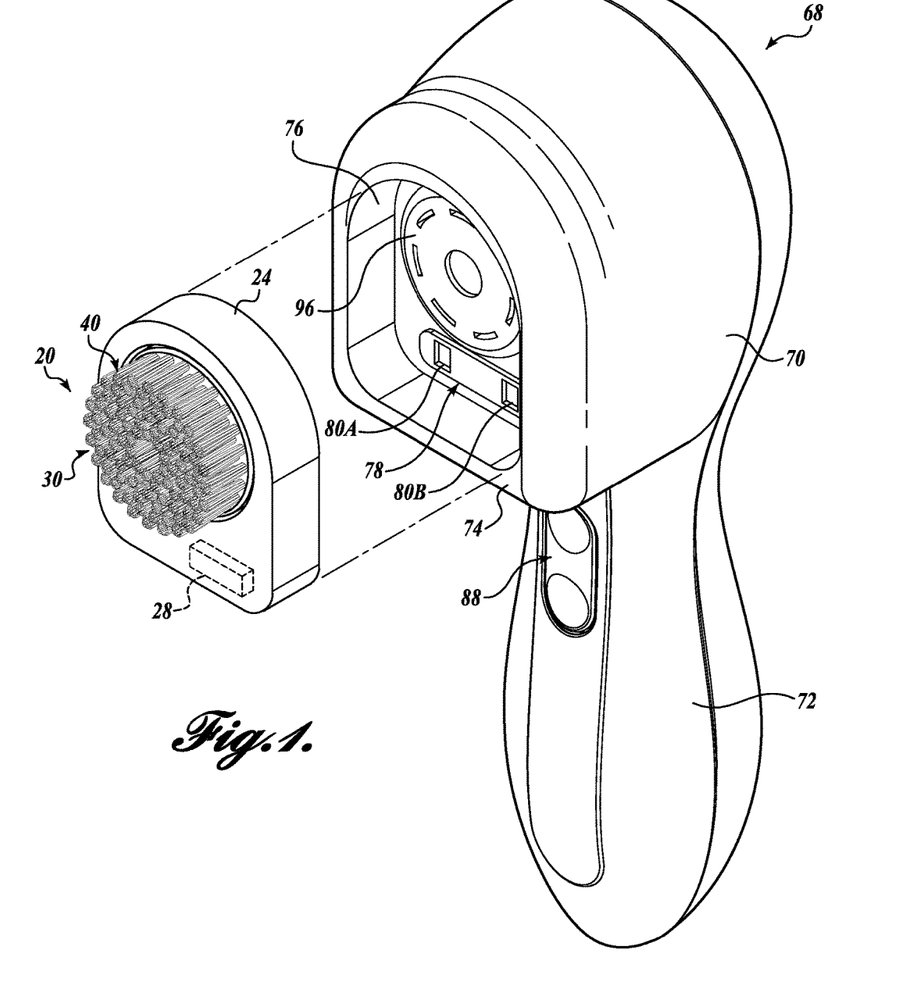
FIG. 1 is a perspective view of one example of a workpiece separated from one example of a personal care appliance, both formed in accordance with aspects of the present disclosure.
Figure 2A:
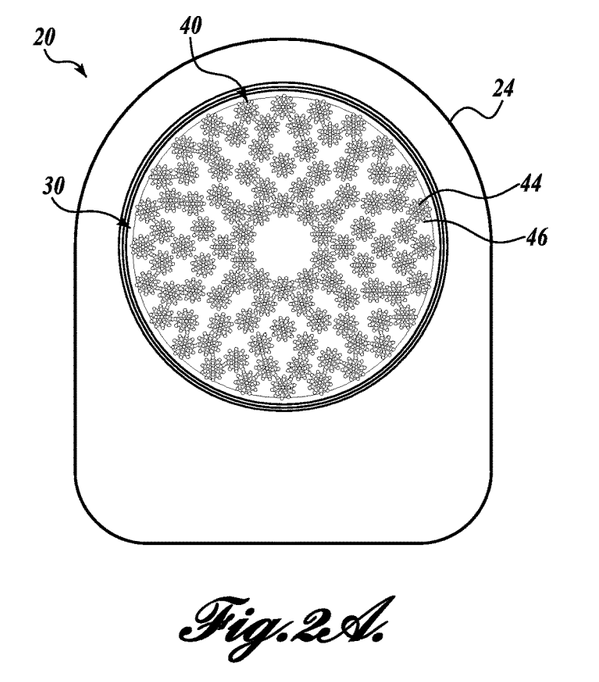
FIGS. 2A-2B are front and rear views of the workpiece of FIG. 1.
Figure 2B:
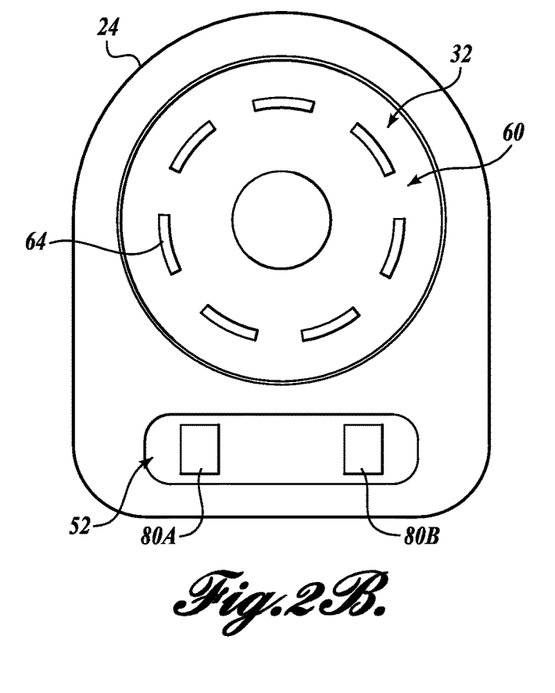

Turning now to FIG. 1, there is shown one example of a treatment workpiece, generally designated 20, formed in accordance with aspects of the present disclosure. The workpiece 20 is suitable for use with a non-powered appliance, such as appliance 68. As shown in FIGS. 1 and 2A-2B, the workpiece 20 includes an outer housing 24 that carries a battery 28 and a treatment device 30. The treatment device 30 is configured to interface directly or indirectly with the appliance 68 at a first or inner end 32 and in some embodiments is movable with respect to the appliance 68. Movement of the treatment device 30 in these embodiments may include but is not limited to oscillating, reciprocating, rotating, elliptical or orbital motion. In the embodiment shown, the treatment device 30 has a generally cylindrical body, although other shapes (e.g., triangular, elliptical, lobular, square, etc.) may be employed. The housing 24 and one or more components of the treatment device 30 can be constructed out of plastic, such as nylon, polypropylene, polyurethane, polyethylene, etc., although other materials may be utilized, including lightweight metals, such as aluminum, titanium, etc.

The treatment device 30 also includes a treatment applicator 40 disposed opposite the first or inner end 32. In the embodiment shown, the treatment applicator 40 is in the form of a plurality of tufts 44. The tufts 44 are spaced apart from one another and include a plurality (e.g., 40-180) of bristles 46. It will be appreciated that other devices/applicators of the treatment and non-treatment type are within the scope of the claimed subject matter. For example, treatment devices configured to deliver, via power supplied from the battery 28, one or more treatments, such as light, sound, magnetic or RF treatment, iontophoresis, phonophoresis, etc., and combinations thereof, may be practiced with embodiments of the present disclosure. In some embodiments, the treatment device can combine a plurality of tufts with one or more other treatment functions, such as light, heat, sound, magnetic or RF treatment, iontophoresis, phonophoresis, just to name a few. In other embodiments, the applicator can include a plurality of tufts and the housing can carry one or more treatment devices configured to provide one or more of the aforementioned treatments via power from battery 28.

Still referring to FIG. 1, the workpiece 20 also includes a battery 28 for providing a suitable supply of power to a motorized, powerless appliance, such as appliance 68. In some embodiments, the battery 28 is configured to provide sufficient energy to allow for at least one complete cycle of use of the workpiece 20 and the associated appliance 68. For example, in some embodiments where the treatment workpiece 20 is a brush head, the battery 28 can be configured with a capacity to provide at least two (2) or more minutes of brush time at an average current rate of 1.5 amps. As a result, the battery 28 in these embodiments includes a storage capacity of about 50 mAh or greater. The battery 28 may also be configured to be recharged quickly, for example, within 180 seconds or less. One example of a battery that may be practiced with embodiments of the present disclosure is the N130.1S.25V1 lithium ion battery from Turnigy. This battery has a capacity of 130 mAh, can be discharged at a rate of up to 25 C, and can be charged at a rate of up to 15 C.

It will be appreciated that the characteristics (e.g., capacity, discharge rate, charging rate, etc.) of the battery 28 can be selected based on the intended application of the workpiece. Thus, for applications having longer use cycle times, or require higher torque, etc., the battery 28 may be configured with larger capacities, higher discharge rates, etc.

In accordance with one aspect of the present disclosure, examples of the workpiece 20 may include a battery configured with a sufficient capacity to provide up to, for example, 90 treatment cycles or greater. In such embodiments, the battery 28 is a fuel cell, such as a Solid Oxide Fuel Cell (SOFC). One example of a fuel cell that may be employed in the workpiece 20 is commercially available from Lilliputian Systems, Inc. In some embodiments, the fuel cell can be non-rechargeable. In these embodiments and others, the capacity of the fuel cell is selected for correspondence with the recommended treatment applicator replacement period. For example, due to the accumulation of dirt and make-up, bristle damage, etc., a bristled workpiece may have a recommended replacement period of approximately 90 days. Accordingly, the capacity of the fuel cell can be selected to provide 90 two minute use cycles. After the energy of the fuel cell is drained, the workpiece 20 can then be replaced with a new workpiece having a full or near full capacity fuel cell.

The workpiece 20 further includes an electrical interface 52 disposed on the back side of the housing 24, as shown in FIG. 2B. In some embodiments, the electrical interface 52 includes first and second conductive contacts 80A and 80B. In other embodiments, the electrical interface 52 includes an inductive coupling. In any case, the electrical interface 52 is configured and arranged so as to be electrically coupled to the cooperating electrical workpiece interface of the appliance/charger when the workpiece 20 is coupled thereto. It will be appreciated that other suitable electrical interfaces may be practiced with embodiments of the present disclosure.

The workpiece 20 further includes a mechanical interface 60 configured to physically couple the workpiece to the appliance 68. Any suitable mechanical interface can be practiced with embodiments of the present disclosure to provide either tool or tool-less techniques for selectively attaching the workpiece 20 to a personal care appliance, such as appliance 68, in a manner that: (1) provides motion to the treatment device 30; and (2) maintains the connection between the treatment device 30 and the drive motor assembly 84 (see FIG. 4). For example, in some embodiments, the treatment device 30 includes a coupling 64 configured to cooperatingly connect to a drive boss 96 (See FIG. 1) of an associated drive assembly in a manner that transmits motion to the treatment device 30 while fixedly securing the treatment device 30 thereto. In other embodiments, the mechanical interface 60 may include coupling 64 on the treatment device 30 and a coupling formed on or by the housing 24 for selectively securing the housing 24 to the appliance 68. In the example shown in FIG. 1, the coupling of the housing 24 may include the shape of the outer perimeter of the housing, which can frictionally fit into a cooperatingly configured socket 78 of the appliance 68. To aid in the securement of the workpiece 20 to the appliance 68, a rib/channel arrangement can be employed. In any case, it will be appreciated that when the mechanical interface couples the workpiece 20 to the personal care appliance 68, the electrical interface 52 connects in electrical communication with the corresponding electrical workpiece interface of the personal care appliance 68.

As briefly described above, the workpiece 20 is configured to be selectively coupled to a motorized, power-less personal care appliance 68. As was described in some detail above, suitable motorized, powerless personal care appliances that may be employed with embodiments of workpiece 20 do not include any source of power. In that regard, one example of a power-less, motorized personal care appliance 22 that may be selectively coupled to the workpiece 20 to impart motion to the treatment device 30 will now be described in some detail with reference to FIGS. 1 and 4. While the power-less, motorized personal care appliance 68 is one type of appliance that can be practiced with embodiments of the present disclosure, it will be appreciated that the workpiece 20 is suitable for use with a wide range of power-less oscillatory, rotational, and reciprocating motion generating devices.

Figure 4:
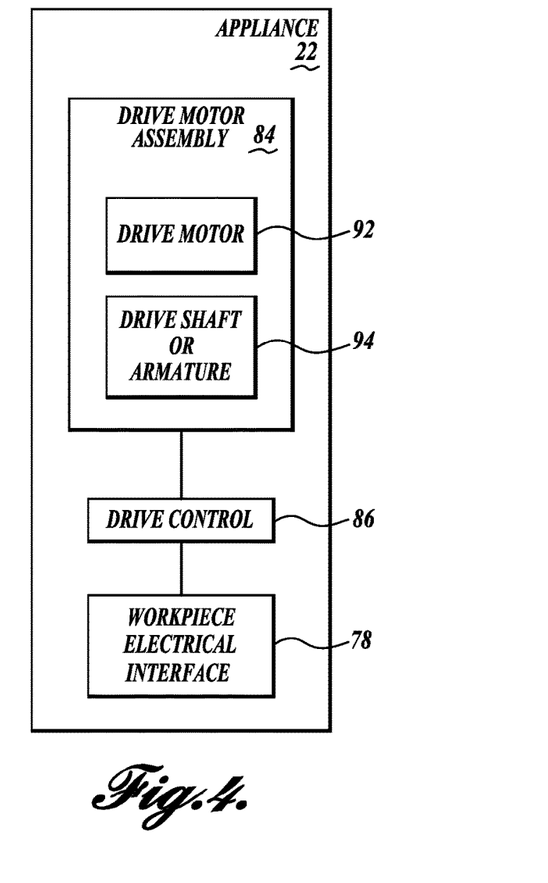
FIG. 4 is a block diagram of one example of the appliance of FIG. 1.

Turning now to FIGS. 1 and 4, there is shown one example of the power-less, motorized appliance 68. As shown in FIG. 1, the appliance 68 includes a body 70 having a handle portion 72 and a workpiece attachment portion 74. The workpiece attachment portion 74 is configured with a socket 76 to interact with the housing 24 in order to selectively attach the workpiece 20 to the appliance 68. Additionally, the coupling 64 of the workpiece 20 is configured to selectively attach to the drive boss 96 (see FIG. 1), which is located in the interior of socket 76. The workpiece attachment portion 74 is also provided with an electrical workpiece interface 78, which is configured to achieve electrical communication with the electrical interface 52 when the workpiece 20 is selectively attached thereto. In some embodiments, the electrical workpiece interface 78 may include but is not limited to electrical contacts 80A and 80B, inductive couplings, etc.

The appliance body 70 houses the operating structure of the appliance. As shown in block diagrammatic form in FIG. 4, the operating structure in one embodiment includes a drive motor assembly 84 and a drive control 86 that includes an on/off button 88 (See FIG. 1). When the workpiece 20 is attached to the appliance 68, the on/off button 88 is configured and arranged to selectively deliver power from the battery 28 of workpiece 20 to the drive motor assembly 84 of the appliance 68. In some embodiments, the drive control 86 may also include power adjust or mode control buttons coupled to control circuitry, such as a programmed microcontroller or processor, which is configured to control the delivery of power to the drive motor assembly 84. The drive motor assembly 84 in some embodiments includes an electric drive motor 92 that drives the workpiece 20 via a drive shaft/armature 94 and drive boss 96.

When the workpiece 20 is mounted in the socket 76 of the workpiece attachment portion 74, the drive motor assembly 84 is configured to impart motion to the workpiece 20. In some embodiments, the drive motor assembly 84 may be configured to operate the workpiece 20 at sonic frequencies, typically in the range of 40-350 Hz, oscillating the workpiece 20 back and forth within a range or amplitude of 3-45 degrees. In some embodiments, as will be described in more detail below, the workpiece 20 can be operated in loaded or unloaded conditions at frequencies from about 80 Hz to about 220 Hz and with a range or amplitude of about 6 degrees to about 20 degrees. It will be appreciated that the operation frequency and oscillation amplitude imparted to the workpiece 20 by the drive motor assembly 84 could be varied, depending in part on its intended application and/or characteristics of the workpiece, such as its inertial properties, etc.

In accordance with another aspect of the present disclosure, a charger, generally designated 100, is provided in order to recharge the one or more batteries 28 in some embodiments of the workpiece 20. In that regard, attention is directed to FIGS. 5 and 6, where there is shown one example of a charger 100 in accordance with aspects of the present disclosure. The charger 100, shown in this embodiment in the form of a wall charger, includes charging circuitry 104, an electrical outlet interface 108, an electrical workpiece interface 112, and a mechanical workpiece interface 116, as shown in the perspective view of FIG. 5 and the block diagram of FIG. 6.

The mechanical workpiece interface 116 is configured to physically couple with or allow mounting of the workpiece 20. Any suitable mechanical workpiece interface 116 can be practiced with embodiments of the present disclosure. In the embodiment shown, the mechanical interface 116 includes a socket 120 cooperatingly configured to receive the rear end of the workpiece 20 in a supporting and optional frictionally engaging manner. Other configurations can be also used. Disposed within the socket 120 is the electrical workpiece interface 112. In some embodiments, the electrical workpiece interface 112 includes first and second conductive contacts 124A and 124B. In other embodiments, the electrical workpiece interface 112 includes an inductive coupling. Other configurations can be also used. In any case, the electrical workpiece interface 112 is positioned so as to be electrically coupled to the cooperating workpiece electrical interface 52 (hidden in FIG. 5) when the workpiece 20 is inserted into the socket 120.

Figure 5:
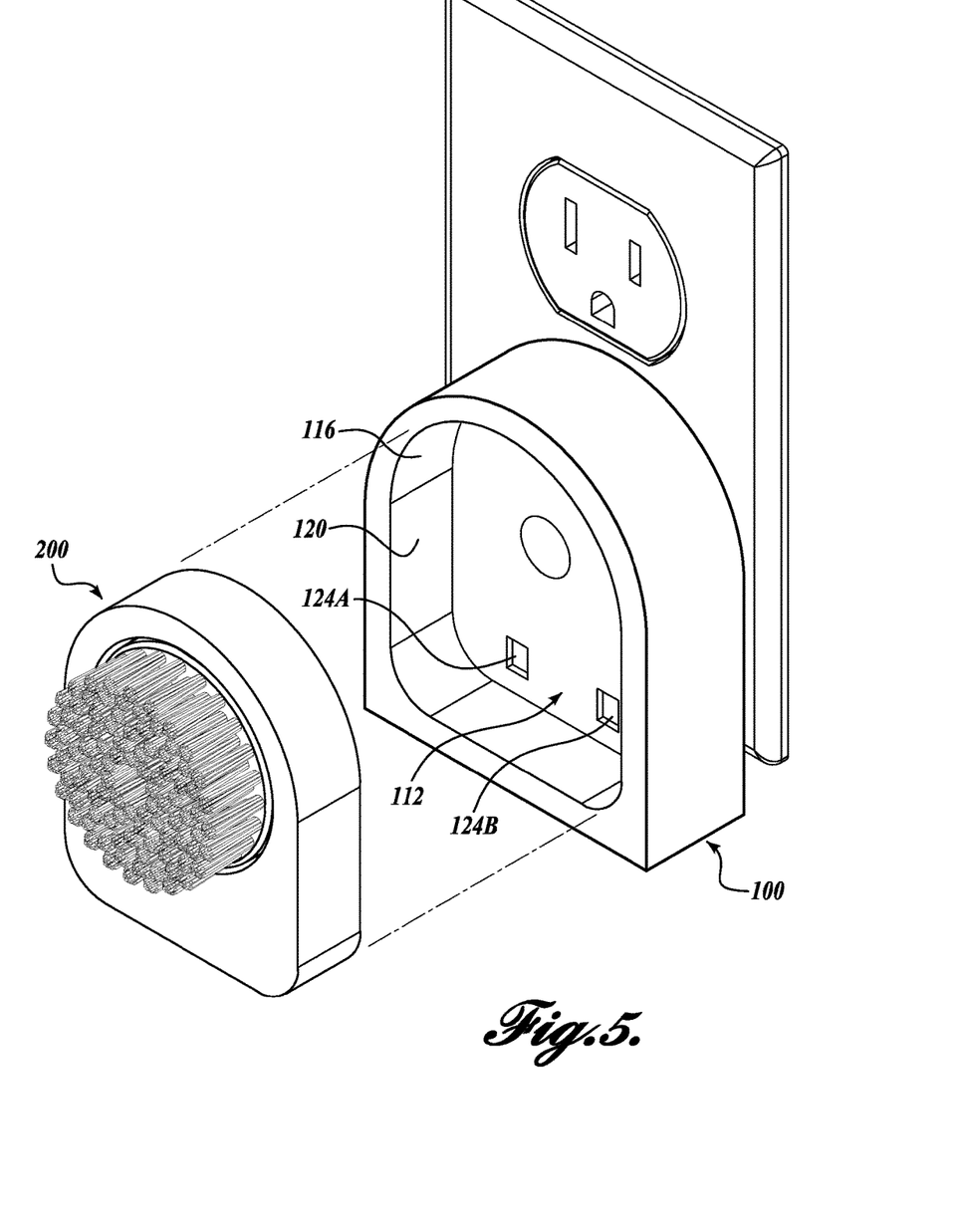
FIG. 5 is a perspective view of one example of a charger in accordance with aspects of the present disclosure, the charger suitable for recharging the workpiece of FIG. 1.
Figure 6:
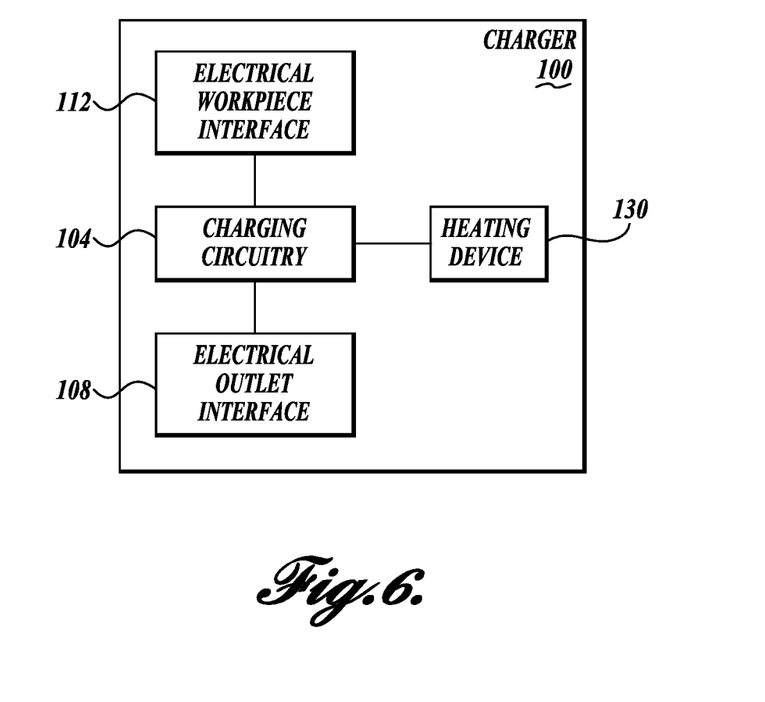
FIG. 6 is a block diagram of one example of the electrical components of the charger of FIG. 5.

The charging circuitry 104 is coupled in electrical communication between the electrical outlet interface 108 and the electrical workpiece interface 112. The charging circuitry 104 is configured to control recharging of the battery 28 when the charger 100 is electrically coupled to a source of mains power (e.g., wall outlet, power strip outlet, etc.) via electrical outlet interface 108, and the workpiece 20 is mechanically and electrically coupled to the charger 100 via interfaces 112 and 116. In some embodiments, the charging circuitry 104 is configured to provide at least a 1.5 amps or greater recharge current to the battery 28. Other charging current values can be also used.

It is known that the process of converting mains power to stored battery power is less than 100% efficient. In that regard, at least a portion of the lost energy shows up as heat. In embodiments of the present disclosure, such generated heat is employed as an aid to drying parts of the workpiece 20. For example, the treatment applicator 40 of the workpiece in some embodiments are used in wet conditions, such as face cleansing. Wet workpieces are a good substrate for the formation and growth of mold, flora, fauna, etc. In this regard, the heat generated from charging the battery 28 can be transferred through conduction for drying the applicator 40.

Figure 3:
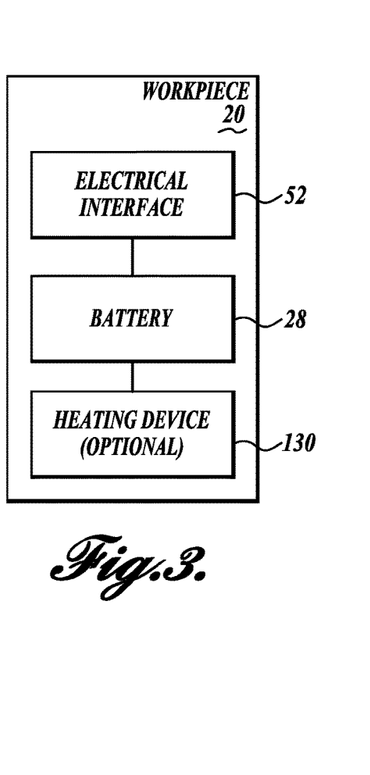
FIG. 3 is a block diagram of one example of the electrical components of the workpiece of FIGS. 2A-2B.

In other embodiments, the charger 100 may optionally include a heating device 130, as shown in FIG. 6. In some embodiments, the heating device 130 is coupled to the charging circuitry 104 in such a manner that the heating device 130 only receives power when the workpiece 20 is coupled to the charger 100. In this regard, the charging circuitry 104 can include auto-sensing circuitry to carry out this functionality, or a simple switch, such as proximity sensor or push switch, can be activated when the workpiece is mounted in the charger 100. The heating device 130 can include a resistive heating element or other type of heating generating means for generating heat when electrical power is supplied thereto. The heating device 130 can be placed in contact with, for example, a surface of the outer housing of the charger 100 that contacts the workpiece 20 when the workpiece 20 is coupled to the charger 20. It will be appreciated that the heating device 130 could be additionally or alternatively disposed within the workpiece 20, as shown in FIG. 3.

In use, when the workpiece 20 is mounted in the charger 100 and the charger 100 is connected to mains power, the heating device 130 is configured to generate heat. Due to the placement of the heating device 130 and the materials of the charger and workpiece housings, the heat is transferred to the workpiece 20. As a result, a decrease in drying time of the applicator 40 can be realized. In some embodiments, a timing circuit or the like can be employed to turn off the heating device 130 after a preselected time period has expired.

It should be noted that for purposes of this disclosure, terminology such as "upper," "lower," "vertical," "horizontal," "inwardly," "outwardly," "inner," "outer," "front," "rear," etc., should be construed as descriptive and not limiting the scope of the claimed subject matter. Further, the use of "including," "comprising," or "having" and variations thereof herein is meant to encompass the items listed thereafter and equivalents thereof as well as additional items. Unless limited otherwise, the terms "connected," "coupled," and "mounted" and variations thereof herein are used broadly and encompass direct and indirect connections, couplings, and mountings.

The principles, representative embodiments, and modes of operation of the present disclosure have been described in the foregoing description. However, aspects of the present disclosure which are intended to be protected are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the present disclosure, as claimed.

The embodiments of the invention in which an exclusive property or privilege is claimed are defined as follows:

1. A workpiece for use with a non-powered appliance, the workpiece comprising:
   a housing;
   a battery enclosed within the housing;
   a treatment applicator; and
   an electrical interface carried by the housing, the electrical interface configured to be electrically coupled to the non-powered appliance for supplying power from the battery thereto.

2. The workpiece of claim 1, further comprising a treatment device movable with respect to the housing, the treatment device carrying the treatment applicator.

3. The workpiece of claim 1, wherein the treatment applicator includes one or more bristled tufts.

4. The workpiece of claim 3, wherein the workpiece is configured to deliver a treatment selected from a group consisting of light, heat, sound, magnetic or RF treatment, iontophoresis, and phonophoresis.

5. The workpiece of claim 1, wherein the treatment applicator is configured to deliver a treatment selected from a group consisting of light, heat, sound, magnetic or RF treatment, iontophoresis, and phonophoresis.

6. The workpiece of claim 1, further comprising a heating device carried by the housing, the heating device being discrete from the battery.

7. The workpiece of claim 1, wherein the battery is selected from a group consisting of a fuel cell, a capacitor, a condenser, one or more Lithium ion cells (Li-ion), one or more alkaline cells, one or more nickel-cadmium (NiCd) cells, one or more nickel-metal hydride (NiMH) cells, and one or more lead-acid cells.

8. The workpiece of claim 1, wherein the battery is configured with a power capacity for at least one treatment applied by the treatment applicator.

9. The workpiece of claim 1, wherein the battery is configured with a power capacity that is dependent on a recommended replacement period of the workpiece.

10. The workpiece of claim 1, further comprising a mechanical interface configured so as to allow the workpiece to be detachably connected to the non-powered appliance.

11. An apparatus, comprising:
    a non-powered appliance including a drive motor and a workpiece electrical interface; and
    a workpiece selectively mounted to the non-powered appliance, wherein the workpiece includes a treatment applicator, a battery enclosed within a housing of the workpiece, and an electrical interface configured to be coupled to the workpiece electrical interface when the workpiece is mounted to the non-powered appliance for supplying power from the battery to the drive motor.

12. The apparatus of claim 11, wherein the treatment applicator includes one or more tufts of bristles.

13. The apparatus of claim 12, wherein the workpiece further includes a heating device.

14. The apparatus of claim 12, further comprising a treatment device configured for movement by the drive motor, the treatment device carrying the treatment applicator.

15. The apparatus of claim 14, wherein the treatment applicator includes a plurality of bristled tufts and wherein the workpiece is configured to deliver, via power from the battery, a treatment selected from a group consisting of light, heat, sound, magnetic or RF treatment, iontophoresis, and phonophoresis.

16. The apparatus of claim 11, further comprising a charger that includes a workpiece interface for selective mounting of the workpiece, an electrical outlet interface configured to receive power from an electrical outlet, and a workpiece electrical interface coupled to the electrical outlet interface, the charger configured to recharge the battery when the charger receives power from the electrical outlet and the workpiece is mounted to the charger.

17. The apparatus of claim 11, wherein the non-powered appliance further includes a workpiece mechanical interface, and wherein the workpiece further comprises a mechanical interface configured to be detachably connected to the workpiece mechanical interface of the non-powered appliance.

* * * * *